United States Patent
Heynen et al.

(10) Patent No.: US 6,507,756 B1
(45) Date of Patent: Jan. 14, 2003

(54) DUAL CHAMBER PACING SYSTEM HAVING TIME-ADAPTIVE AV DELAY

(75) Inventors: Henri G. M. Heynen, Geleen (NL); Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/542,258

(22) Filed: Apr. 3, 2000

(51) Int. Cl.$^7$ ................................. A61N 1/368
(52) U.S. Cl. ............................... 607/9; 607/25
(58) Field of Search ........................ 600/509; 607/4, 607/5, 9, 11, 123, 25

(56) References Cited

U.S. PATENT DOCUMENTS

| | | | |
|---|---|---|---|
| 4,428,378 A | 1/1984 | Anderson et al. ...... 128/419 PG |
| 4,890,617 A | 1/1990 | Markowitz et al. ... 128/419 PG |
| 5,144,949 A | 9/1992 | Olson ................... 128/419 PG |
| 5,334,220 A | 8/1994 | Sholder ...................... 607/9 |
| 5,340,361 A | 8/1994 | Sholder ...................... 607/24 |
| 5,507,782 A | 4/1996 | Kieval et al. ................ 607/9 |
| 5,534,016 A | 7/1996 | Boute ........................ 607/9 |
| 5,534,506 A | 7/1996 | Morgan et al. ............. 514/185 |
| 5,626,620 A | 5/1997 | Kievel et al. ................ 607/9 |
| 5,626,623 A | 5/1997 | Kieval et al. ................ 607/23 |
| 5,716,383 A | * 2/1998 | Kieval et al. ................ 607/9 |
| 5,749,906 A | 5/1998 | Kieval et al. ................ 607/9 |
| 5,836,989 A | * 11/1998 | Shelton ...................... 607/27 |

* cited by examiner

Primary Examiner—Jeffrey R. Jastrzab
Assistant Examiner—Frances P. Oropeza
(74) Attorney, Agent, or Firm—Thomas F. Woods; Eric R. Waldkoetter; Tom G. Berry

(57) ABSTRACT

Rate responsive pacing systems that employ a time-dependent AV delay in the pacing hearts in Congestive Heart Failure (CHF) with Dilated Cardiomyopathy (DCM) (a CHF/DCM heart) during a post-implant Time-Adaptive period are disclosed. A starting or initial AV delay is set to an intrinsic AV delay time interval exhibited by the patient's heart at the time of implant. A chronic AV delay is then set to a therapeutic AV delay time interval that is shorter than the intrinsic AV delay time interval and alleviates symptoms of the CHF/DCM heart. A Time-Adaptive AV delay (TA-AV delay) is employed during a post-implant Time-Adaptive period that gradually changes the initial AV delay to the chronic AV delay at the end of the post-implant Time-Adaptive period.

32 Claims, 10 Drawing Sheets

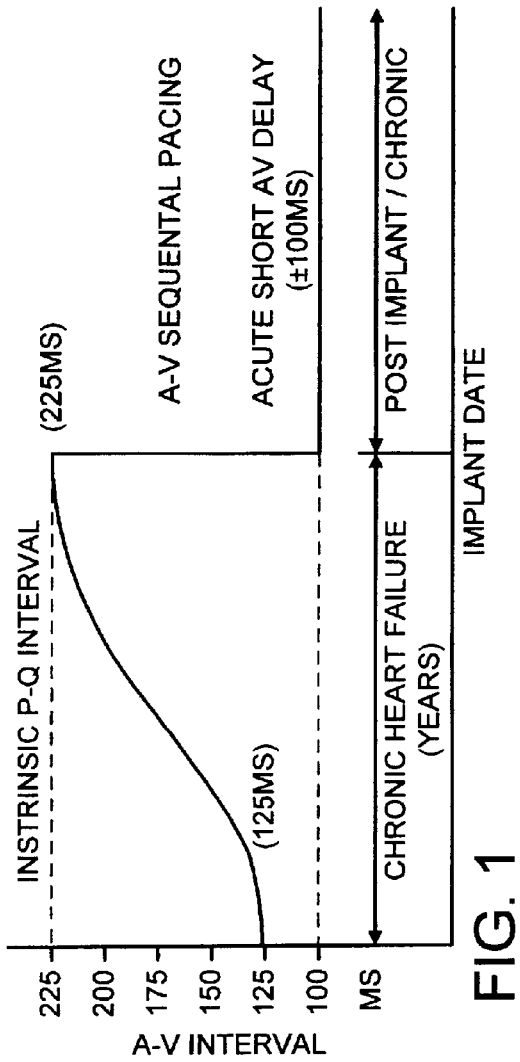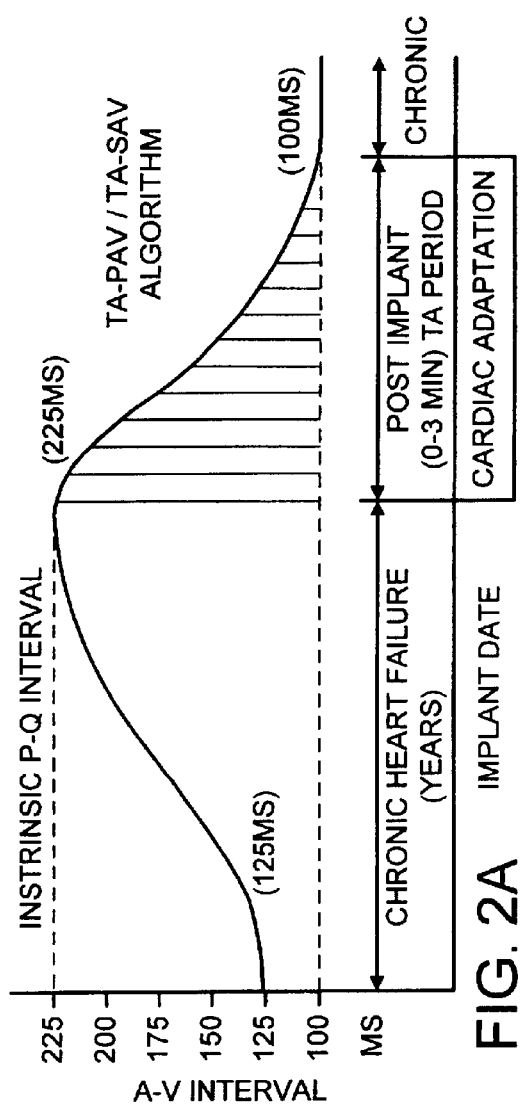
FIG. 1
FIG. 2A

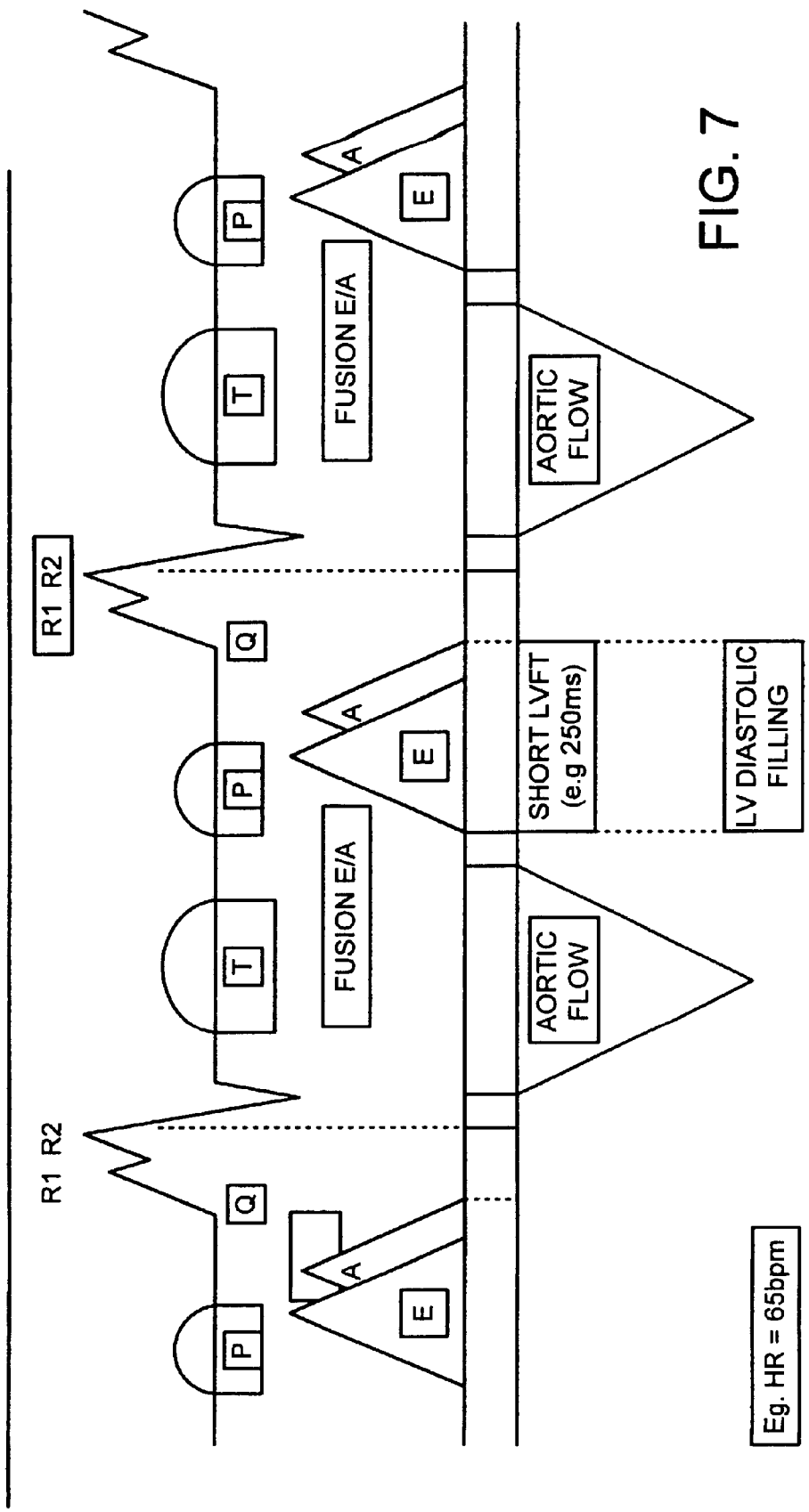

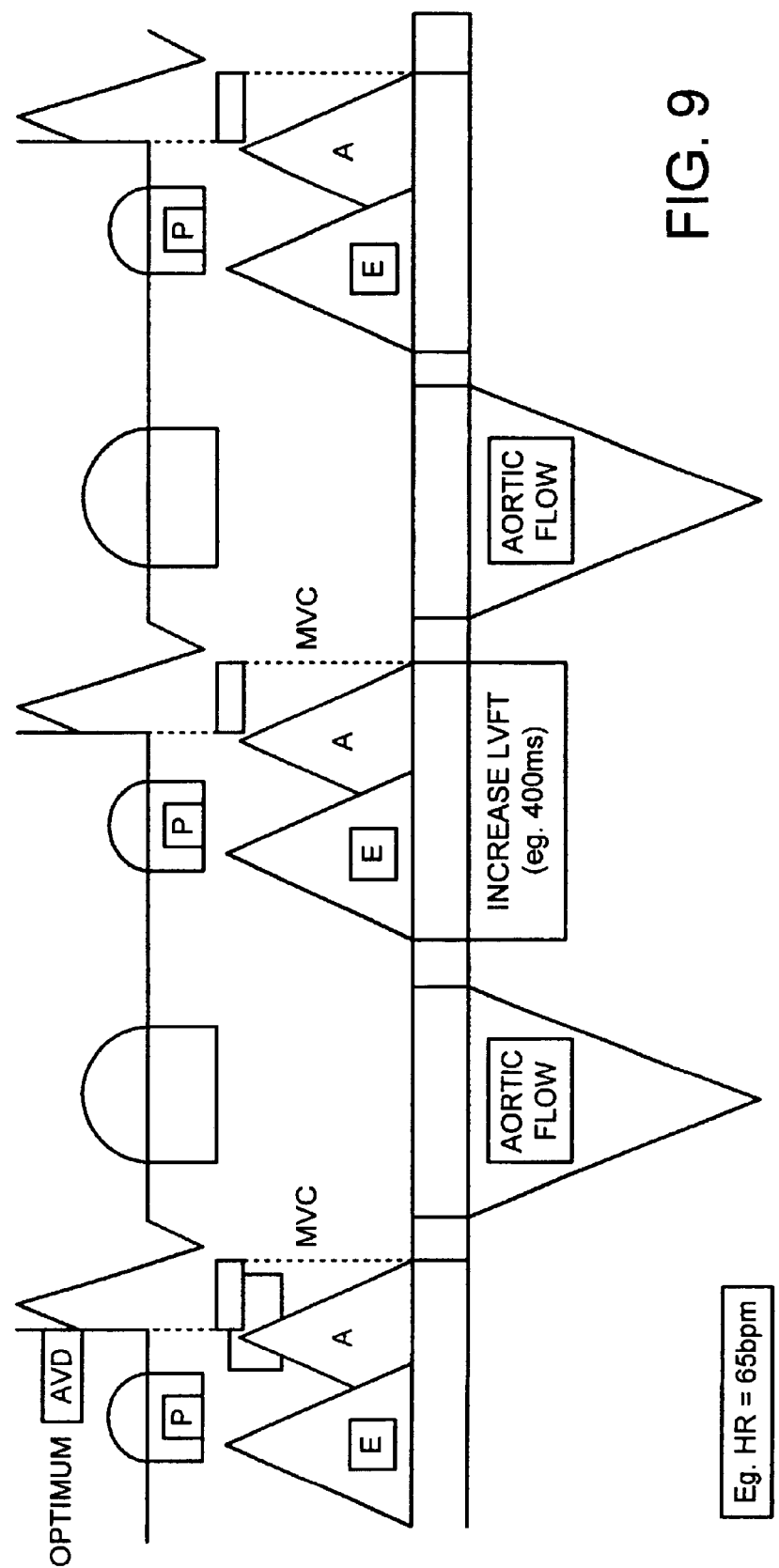

DUAL CHAMBER PACING SYSTEM HAVING TIME-ADAPTIVE AV DELAY

FIELD OF THE INVENTION

The present invention relates to dual chamber pacing systems, including rate responsive pacing systems, and more particularly to the employment of a time-dependent AV delay for pacing hearts in Congestive Heart Failure (CHF) with Dilated Cardiomyopathy (DCM).

BACKGROUND OF THE INVENTION

Dual chamber pacing systems operating in the multi-programmable, DDD and DDDR pacing modes have been widely adopted in implantable dual chamber pacemakers and certain implantable cardioverter/defibrillators (ICDs) for providing atrial and ventricular (AV) synchronized pacing on demand. A DDD pacemaker implantable pulse generator (IPG) includes an atrial sense amplifier to detect atrial depolarizations or P-waves and generate an atrial sense event (A-EVENT) signal, a ventricular sense amplifier to detect ventricular depolarizations or R-waves and generate a ventricular sense event (V-EVENT) signal, atrial and ventricular pacing pulse generators providing atrial and ventricular pacing (A-PACE and V-PACE) pulses, respectively, and an operating system governing pacing and sensing functions. If the atria fail to spontaneously beat within a pre-defined time interval (atrial escape interval), the pacemaker supplies an A-PACE pulse to the atria through an appropriate lead system. The IPG supplies a V-PACE pulse to the ventricles through an appropriate lead system at the time-out of an AV delay timed from a preceding A-EVENT or generation of an A-PACE pulse unless a non-refractory V-EVENT is generated in response to an R-wave during the AV delay. Such AV synchronous pacemakers which perform this function have the capability of tracking the patient's natural sinus rhythm and preserving the hemodynamic contribution of the atrial contraction over a wide range of heart rates.

The rate-adaptive DDDR pacing mode functions in the above-described manner but additionally provides rate modulation of a pacing escape interval between a programmable lower rate and an upper rate limit (URL) as a function of a physiologic signal or rate control parameter (RCP) developed by one or more physiologic sensors and related to the need for cardiac output. In the DDDR pacing mode, reliance on the intrinsic atrial heart rate is preferred if it is appropriately between the URL and the programmed lower rate. At times when the intrinsic atrial rate is inappropriately high, a variety of "mode switching" schemes for effecting switching between tracking modes and non-tracking modes (and a variety of transitional modes) based on the relationship between the atrial rate and the sensor derived pacing rate have been proposed as exemplified by commonly assigned U.S. Pat. No. 5,144,949, incorporated herein by reference in its entirety.

The DDD and DDDR pacing modes were initially perceived to be of greatest benefit to cardiac patients whose hearts have an intact sinoatrial (SA) node that generates the atrial depolarizations detectable as P-waves, but also suffer defective A-V conduction, or AV block, wherein the ventricles fail to depolarize in synchrony with the atria. The DDD pacing mode paces the ventricles in synchrony with the atria after a timed out AV delay and is generally adequate to restore cardiac output for sedentary patients. Active patients with Sick Sinus Syndrome (SSS) have an atrial rate which can be sometimes appropriate, sometimes too fast, and sometimes too slow. For SSS patients, the DDDR pacing mode provides some relief by pacing the atria and ventricles at a physiologic rate determined by an algorithm responsive to the RCP indicative of the patient's metabolic needs.

A loss of A-V electrical and mechanical synchrony can result in series of asynchronous atrial and ventricular depolarizations at independent rates that periodically result in an atrial depolarization that closely follows a ventricular depolarization. When this occurs, the left atrium contracts against a closed mitral valve, resulting in impeded venous return from the pulmonary vasculature due to increased atrial pressure and possibly even retrograde blood flow into the pulmonary venous circulation. As a result, the volume and pressure in the pulmonary venous circulation rise. Increased pulmonary pressures may lead to pulmonary congestion and dyspnea. Distention of the pulmonary vasculature may be associated with peripheral vasodilation and hypotension. In addition, the concomitant atrial distention is associated with increased production of atrial natriuretic factor and increases the susceptibility to atrial arrhythmias and possibly rupture of the atrial wall. Finally, turbulence and stagnation of blood within the atrium increase the risk of thrombus formation and subsequent arterial embolization. Maintenance of AV mechanical synchrony is therefore of great importance as set forth in greater detail in commonly assigned U. S. Pat. No. 5,626,623, incorporated herein by reference in its entirety.

Theoretically, AV synchrony is best maintained during dual chamber cardiac pacing by setting the AV delay interval in a physiological range related to the spontaneous atrial rate or the sensor derived rate, depending on which is the controlling pacing mode. However, while "physiological" AV delays may ensure right heart AV electrical synchrony, in patients with significant interatrial and/or interventricular conduction delays, left heart electrical and mechanical synchrony, and thus hemodynamic performance, may be significantly compromised.

The maintenance of AV mechanical synchrony is of vital importance in patients with compromised cardiac function, including CHF, DCM, hypertrophic cardiomyopathy, hypertensive heart disease, restrictive cardiomyopathy, and other disorders that are characterized by significant diastolic dysfunction. In such patients, passive ventricular filling is reduced due to poor ventricular compliance and incomplete or delayed relaxation. Consequently, there is increased reliance on atrial contraction for ventricular filling sufficient to achieve adequate stroke volume and maintain low atrial and pulmonary pressure.

Carefully controlled AV delays have been found to be beneficial to increase cardiac output of hearts of certain patients that exhibit cardiomyopathy and forms of CHF, and in particular Hypertrophic Obstructive Cardiomyopathy (HOCM). HOCM is characterized by a narrowed left ventricular outflow tract (LVOT), which causes a significant increase in the left ventricular end systolic pressure. The narrowed LVOT is caused by an increased thickness of the interventricular septum which obstructs blood flow during systole, the time of cardiac ejection.

Symptomatic improvement of patients with HOCM can be obtained in some cases with the use of standard pharmacotherapy. However, drugs in use for this therapy have disadvantages which have been cited in the literature. Likewise, surgical intervention, e.g., septal myectomy or mitral valve replacement, is another optional treatment. However, such surgical treatments carry a significant operative mortality and have not been shown to alter the natural history of the disease. See, for example, "Permanent Pacing As Treatment For Hypertrophic Cardiomyopathy," by Kenneth M. McDonald et al., *American Journal of Cardiology*, Vol. 68, pp. 108–110, July 1991.

The value of dual chamber cardiac pacing and treatment of patients suffering from HOCM has been recognized in the literature. Studies have indicated that patients suffering from HOCM may benefit from a specific mode of dual chamber pacing, wherein a ventricular pacing pulse is delivered in timed synchrony with the sensed or paced atrial depolarization. Pacing the right ventricular apex before spontaneous atrio-ventricular conduction activates the ventricles is understood to alter the ventricular septal activation pattern. Since the right ventricle is caused to contract first, it pulls the septum toward the right ventricle thereby reducing the LVOT obstruction. The literature uniformly acknowledges the potential advantages of synchronized AV pacing for HOCM patients, stressing the importance of achieving ventricular capture. Causing "complete ventricular capture" is important to obtain the above-described septal movement, while selecting the longest AV delay that results in complete ventricular capture is important in order to maximize the atrial contribution to ventricular filling. See, for example, commonly assigned U.S. Pat. No. 5,507,782, and the literature articles referenced therein. The delivered pacing pulse should provide "pre-excitation," i.e., depolarization of the ventricular apex before the septum. This altered pattern of septal contraction, as well as optimal left ventricular filling, is generally recognized as being important to this mode of pacemaker treatment.

The literature suggests that the AV delay should be set at the longest duration that maintains ventricular capture at different exercise levels. See the above-cited McDonald article. It has been suggested that the AV delay that allows for maximal pre-excitation of the ventricle by the pacing pulse can be selected by determining the AV delay that produces the widest paced QRS complex duration, as seen on a surface electrocardiogram. See, for example, "Impact of Dual Chamber Permanent Pacing in Patients With Obstructive Hypertrophic Cardiomyopathy With Symptoms Refractory to Verapamil and beta.-Adrenergic Blocker Therapy," by Fananapazir et al., *Circulation*, Vol. 8, No. 6, June 1992, pp. 2149–2161.

The prior art techniques for AV synchronous pacing of HOCM patients recognize the necessity to periodically evaluate the pacing AV delay. The patient's spontaneous atrio-ventricular conduction time generally will change with heart rate, i.e., from rest to exercise. Moreover, simultaneous drug treatment such as beta blockers may also modify A-V conduction time and require renewed evaluation of the AV delay. The importance of periodically making an accurate determination of the optimized pacing AV delay thus takes on significance. If the AV delay is adjusted to a value which is too short, in order to ensure complete ventricular capture, the atrial contribution to ventricular filling may be compromised. However, if the AV delay is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously or periodically adjust the AV delay to optimize it for HOCM therapy. Commonly assigned U.S. Pat. Nos. 5,534,506, 5,626,620, 5,626,623, 5,716,383, and 5,749,906 disclose ways of optimizing the pacing AV delay.

However, AV synchronized pacing of CHF hearts exhibiting DCM (a CHF/DCM heart) do not necessarily benefit from the variable, and typically long AV delay that is determined to be optimal for HOCM patients. Frequently, CHF/DCM hearts exhibit intrinsic A-V (alternatively referred to as P-Q) conduction intervals between 180 ms–260 ms with LBBB patterns or Inter-Ventricular Conduction Delay (IVCD), and widened QRS complexes >120 ms, and also exhibit A-V conduction defects, including 1° AV Block (AVB). In time the 1° AV Block can degenerate to 2° AV Block or 3° AV Block. Widened QRS Complexes (>120 ms), caused either by LBBB, IVCD, or RV paced evoked response, represent a significant delay in LV electrical activation and thus a significant delay in LV mechanical activation. FIG. 7. illustrates the intrinsic cardiac sinus rhythm of a patient's heart (at a 65 bpm heart rate, for example) with intrinsic LBBB, 1° AV block, LA to LV asynchrony, and reduced LV filling time with subsequent fusion of transmitral inflow rapid filling phase (E wave) and active filling phase (A wave).

Optimal AV delay timing is obtained when the onset of LV contraction occurs immediately upon completion of the LA contribution (Left Atrial Kick) in late diastole. At this moment, the LV filling (preload) is maximum, and the Frank Starling Relationship between LV stretch and LV contraction is the greatest. This will result in maximum LV stroke volume ejection, and thus maximum Cardiac Index/Cardiac Output to be realized. To realize this exact Atrial-Ventricular Sequential timing, the AV delay must be fully optimized. FIG. 8. illustrates the cardiac rhythm of a heart having a minor LA to LV asynchrony and sub-optimal, too long, AV delay timing, partial fusion of E and A waves, and increased LV Filling (LVFT). Any delay between the completion of atrial contribution and the start of LV contraction (indicated as δ in FIG. 8), can lead to "Pre-Systolic" mitral regurgitation, resulting in loss of effective LV filling and thus loss of LV stroke volume and reduced cardiac output. In addition, a too long AV delay reduces the diastolic time available for proper LVFT) as observed on the diastolic Transmitral Inflow Pattern, resulting in a fusion (competitive action) of the E wave vs. the A wave of the Mitral Flow Relationship (also shown in FIG. 8.).

FIG. 9. illustrates a desirable exact LA to LV synchrony restored in a cardiac rhythm due to a short, optimized AV delay, LV contraction occurring upon completion of A wave, and maximum diastolic LVFT. A short, optimized AV delay, however, will allow maximum defusion of E and A waves, and a maximum LVFT to be realized at any given heart rate, contributing to increased cardiac output (see FIG. 9). Recent findings of studies of such hearts has determined that each CHF/DCM heart has an optimal short AV delay that generates the highest cardiac output and provides the most physiologic hemodynamics as measured using echocardiography. See, "Effect of pacing chamber and atrioventricular delay on acute systolic function of paced patients with congestive heart failure" by Auricchio A, Stellbrink C, et al., *Circulation* 1999, June 15;99(23):2993–3001.

Short AV delays in the range of 60 ms–140 ms appear to be superior to the 180 ms–240 ms AV delays that have been typically either preset or calculated using the algorithms described above for determining the AV delay for HOCM hearts. Consequently, it is recommended that the AV delays of the implanted DDD and DDDR pacemakers be set to the relatively short AV delays determined in testing the cardiac output at differing AV delays.

But, abruptly commencing AV pacing with such a short AV delay represents a significant change in the function of and load on the CHF/DCM heart wherein, prior to pacing, the ventricles depolarized after a longer intrinsic AV delay.

FIG. 1 illustrates the abrupt change from a chronic, prolonged, intrinsic AV delay of 225 ms, for example, exhibited in a CHF/DCM heart that is well above the normal, healthy heart, intrinsic AV delay of 125 ms. After years of gradually increasing intrinsic AV delay, the patient's heart is subjected to a programmed chronic AV delay of 100 ms, for example, for a sense AV delay (SAV delay) or a pace AV delay (PAV delay) or both.

This means that the heart is suddenly forced to change from a situation with long AV to short AV delay. In the long AV delay situation, the filled left ventricle has more time to let blood flow back into the left atrium before contraction starts (mitral regurgitation), which on the one hand reduces the cardiac output but on the other hand may serve as a kind of 'pressure relief valve' to limit the LV end diastolic pressure, which is extremely elevated in these patients. In the short AV delay situation, the maximum cardiac output requirements (exact synchronized filling of LV, optimal LV filling period, and optimal preloading of LV) are met, but the pressure may become high in the LV that is not 'used' to that.

SUMMARY OF THE INVENTION

The present invention is therefore particularly directed to a method and apparatus for avoiding or alleviating stress of a patient's heart induced by programming a relatively short AV delay in comparison to an intrinsic, prolonged AV delay. In accordance with the present invention, a Time-Adaptive AV delay (TA-AV delay) determining algorithm is started upon implantation of a DDD or DDDR pacing system in a patient having a CHF/DCM heart. At or about the time of implantation, the AV delay is initially set at a relatively long starting or initial AV delay that may be correlated with any intrinsic AV delay that the patient's heart exhibits. Thereafter, the TA-AV delay is incrementally decreased or decrement over a post-implant Time-Adaptive (TA) period of time of hours, days or weeks until a programmed, relatively shorter, AV delay is reached. Then, the programmed, chronic, AV delay is maintained.

The TA-AV delay is either linearly or non-linearly decremented in time interval from the initial AV delay to the chronic AV delay in decrement steps over the post-implant TA period. Preferably, a separate SAV delay is commenced by the A-EVENT signal and a PAV delay is commenced at time-out of an atrial pace escape interval and delivery of the A-PACE pulse. The present invention may be implemented in such a way that the Time-Adaptive feature is programmed on to operate for establishing a TA-SAV delay or a TA-PAV delay or both during the post-implant period.

In this way, the heart gradually adapts to the optimal chronic AV delay and stress is reduced. This gradual process may aid in the remodeling process of the CHF/DCM heart. The process of remodeling is a gradual adaptation of the muscle cells of the heart to a new situation of different wall stresses, volume loading, and/or contraction patterns. Some relevant references include the following: "Asynchronous Electrical Activation Induces Asymmetrical Hypertrophy of the Left Ventricular Wall", by Oosterhout, Prinzen, et al., *Circulation*, 1998;98:588–595; and "Redistribution of myocardial fiber strain and blood flow by asynchronous activation" by Prinzen et al., *American Journal of Physiology*, 1990;259:H300–H308.

Preferably, the TA-AV delay is further modified or altered during the TA period to provide a more physiologic AV delay under certain conditions where a need for increased cardiac output causes the pacing system to increase its pacing rate. In this case, the TA-AV delay is calculated but can be temporarily altered by a rate response pacing algorithm.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a time chart illustrating the current manner of setting an AV delay used in a DDD or DDDR pacing system for pacing a CHF/DCM heart;

FIG. 2A is a time chart illustrating the manner of time-adapting the AV delay used in a DDD or DDDR pacing system for pacing a CHF/DCM heart in accordance with the present invention;

FIG. 7 illustrates an intrinsic cardiac sinus rhythm of a patient's heart with intrinsic LBBB, 1° AV block, LA to LV asynchrony, and reduced LV filling time with subsequent fusion of transmitral inflow rapid filling phase (E wave) and active filling phase (A wave);

FIG. 9 illustrates a desirable cardiac rhythm having exact LA to LV synchrony due to a short, optimized AV delay, LV contraction occurring upon completion of A wave, and maximum diastolic LVFT.

DETAILED DESCRIPTION OF THE PREFERRED EMBODIMENTS

FIG. 1 is a time chart illustrating the current manner of setting an AV delay used in a DDD or DDDR pacing system for pacing a CHF/DCM heart.

Figure 2B:
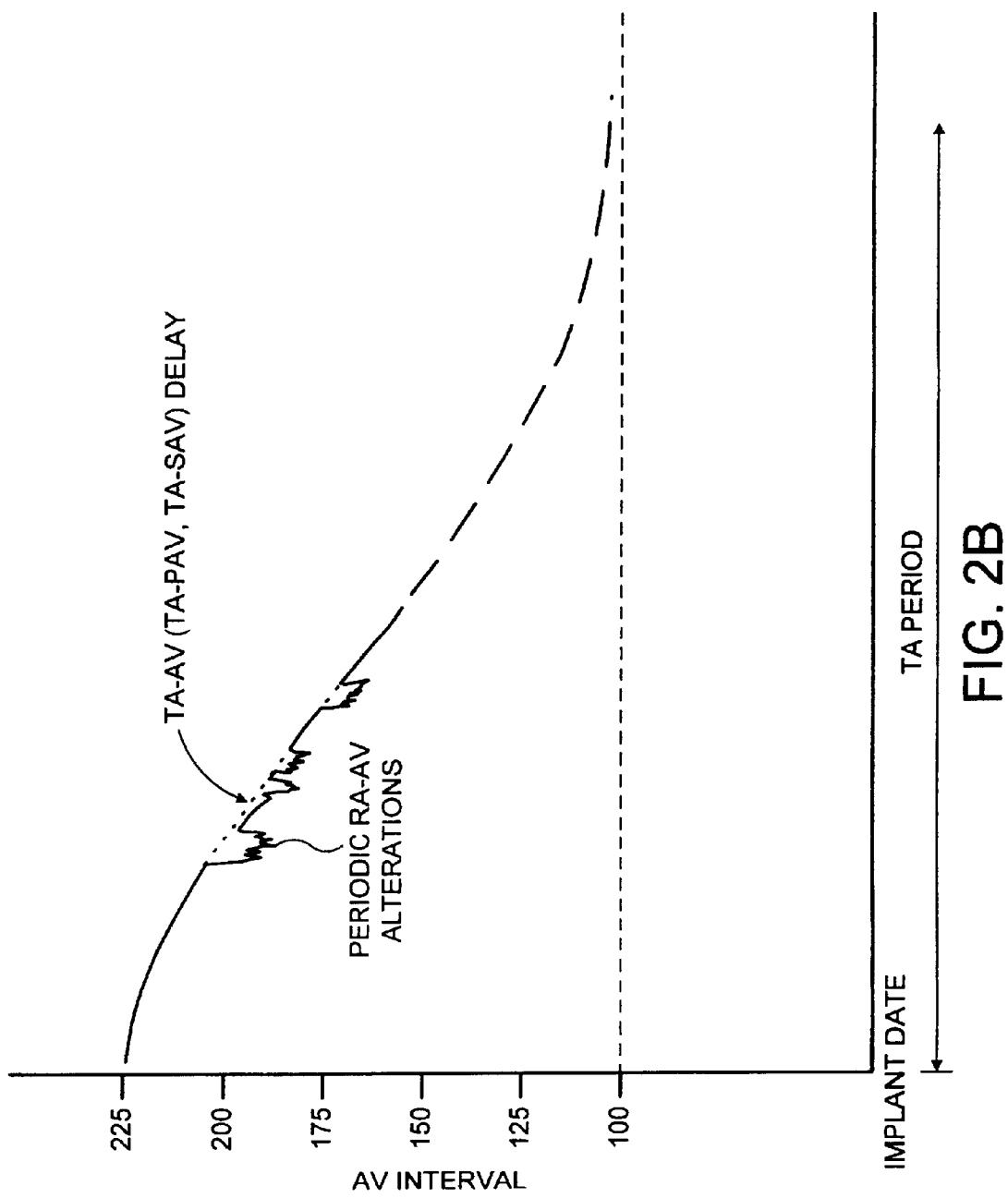
FIG. 2B is a magnification of a portion of the TA-AV delay during the TA period to show incremental reductions in response to a rate adaptation in a rate responsive pacing mode.

FIGS. 2A and 2B illustrate the manner of time-adapting the AV delay used in a DDD or DDDR pacing system for pacing a CHF/DCM heart in accordance with the present invention. The initial or starting AV delay, which may be the SAV delay and/or the PAV delay, is set to be the same or nearly the same length as the intrinsic AV delay, 225 ms in the illustrated case. The AV delay is gradually decreased as a TA-AV delay over a post-implant TA period of hours, days, weeks or months until the programmed, base or chronic, 100 ms, AV delay is reached. This Time-Adaptive shortening of the AV delay allows the heart to grow accustomed to the short AV delay over the TA period and may contribute to remodeling of the heart function. Either a single TA-AV delay is calculated and used during the post-implant period or separate TA-SAV and/or TA-PAV delays are calculated and used over the post-implant period until the expiration of the post-implant period. In practice if the PAV and SAV are set to the same value, then a single TA-AV delay is calculated employed and timed out after either an atrial pace or an atrial sense event.

In a rate responsive (RR) pacing mode, the TA-AV delays can be automatically shortened when an increased activity or heart rate is detected. When such RR modulation of PAV and SAV intervals occurs, these AV delay incremental modulations are superimposed as shown in FIG. 2B on the slow change of the basic TA-AV delay as illustrated in FIG. 2A in accordance with the TA algorithms described further below in reference to FIGS. 6A and 6B.

FIGS. 2A and 2B are simply exemplary of a manner in which the TA-AV (TA-PAV or TA-SAV) delay can be decreased with or without the RR modulation of the TA-AV delay. In typical DDD pacing systems, the PAV and SAV delays are separately programmable and there is typically an offset difference between the PAV and SAV delays when they are either fixed or vary in a RR mode dependent upon the RCP or intrinsic atrial heart rate. For simplicity, only a single AV delay, including the TA-AV delay are shown in FIG. 2A.

The TA-AV delay decrease is effected at specific times (determined by a real time clock) during the post-implant period and typically would be accomplished by decreasing the AV interval by one-half to one or more clock cycle intervals as described further below. The Time-Adaptive curve can therefore take many forms, including a relatively straight ramp a curve, or periodic discrete step or increment decreases.

Figure 3:
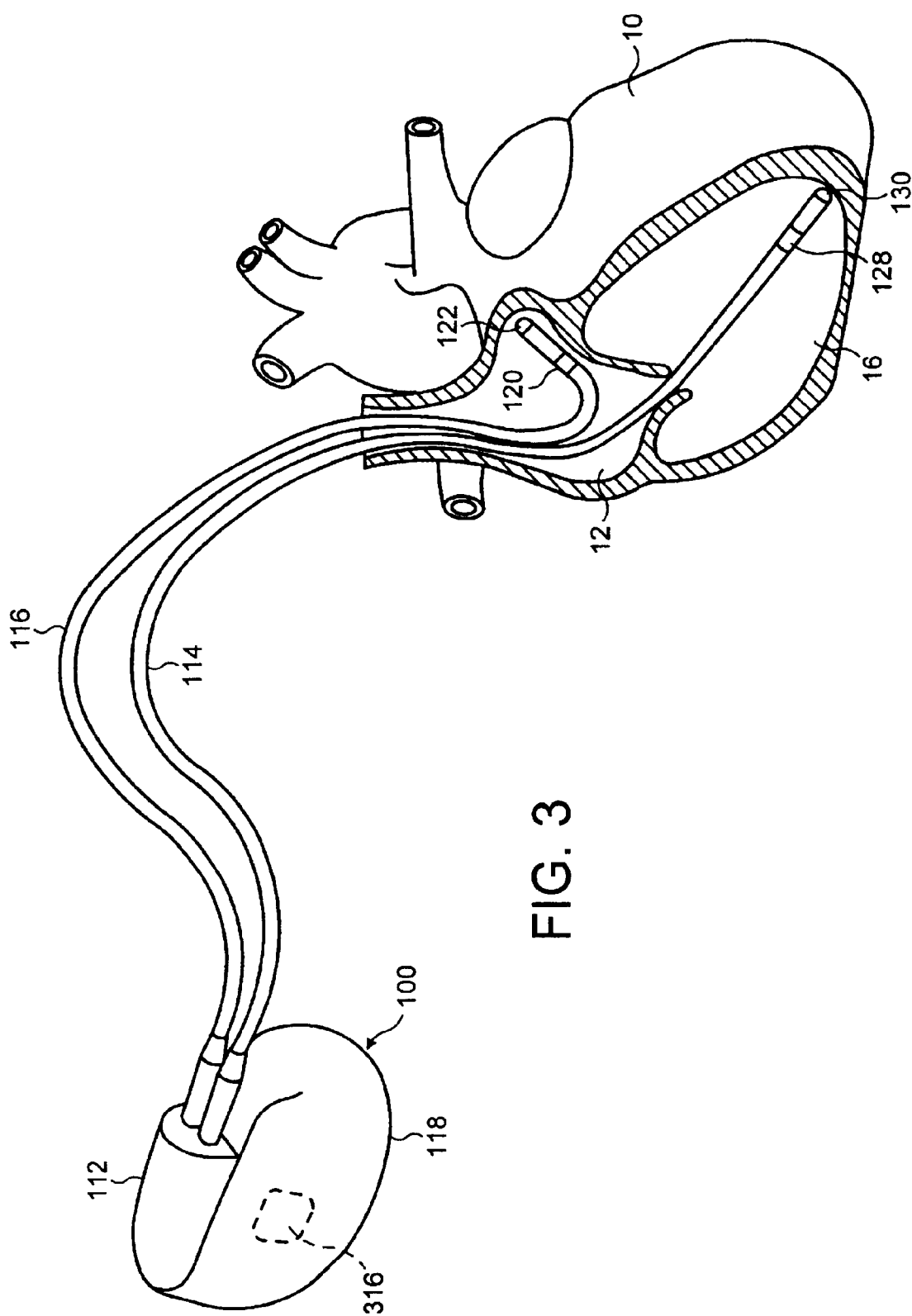
FIG. 3 is a view of one embodiment of an implantable DDD/DDDR pacemaker implanted subcutaneously in a patient's body in which the present invention is advantageously implemented.

The present invention can be incorporated into external and implantable pacing systems, and into both pacemakers and ICDs having dual chamber pacing capability. For example, FIG. 3 depicts the configuration of a typical DDD/DDDR pacing system comprising IPG 100 and unipolar or bipolar right atrial (RA) and right ventricular (RV) leads 114 and 116 (bipolar leads are depicted), in which the present invention may be implemented to synchronously pace the atria and ventricles in a RA-RV sequence. The present invention may also be incorporated into other dual chamber pacing systems employing left atrial (LA) and/or left ventricular (LV) leads for dual chamber pacing using the TA-AV delay in the sequences LA-RV, LA-LV or RA-LV.

The TA-AV delay may also be employed in bi-atrial and bi-ventricular pacing systems having LA and/or r LV leads of the types described, for example, in commonly assigned U.S. Pat. No. 5,902,324 and commonly assigned U.S. patent application Ser. No. 09/067,729 filed Apr. 28, 1998 for MULTIPLE CHANNEL, SEQUENTIAL, CARDIAC PACING SYSTEMS filed in the names of C. Struble et al. The TA-AV delay algorithms of the present invention may be incorporated into such three and four chamber DDD/DDDR pacing systems wherein the pacing sequences can include RA-(RV+LV), LA-(RV+LV), (RA+LA)-RV, (RA+LA)-LV, and (RA+LA)-(RV+LV).

Typically, the DDDR pacing system described below in reference to FIGS. 3–6 comprises a microcomputer controlled, digital controller/timer circuit that defines and times out a V-A interval upon a V-EVENT or V-PACE pulse followed by an AV delay upon an A-EVENT or A-PACE pulse as well as a number of other intervals. Preferably, the SAV delay is commenced by the A-EVENT signal and the PAV delay is commenced upon an A-PACE pulse, and both are set in a Time-Adaptive manner. But the present invention may be implemented in such a way that the Time-Adaptive feature is only programmed on to operate for the setting of the SAV or the PAV or for a single AV delay for both. While the present invention is believed optimally practiced in a DDD or DDDR pacing mode, in some patients there may also be a benefit to practicing the invention in a VDD/DDR or DVI/DVIR pacing mode, depending upon the specific underlying heart condition of the patient. It is contemplated that these features of the invention are most likely to be implemented in either a DDD or DDDR pacemaker IPG or pacing system of an ICD IPG which may be programmed to these alternate pacing modes.

Additional timed intervals include atrial and ventricular sense amplifier blanking periods following delivery of an atrial and/or ventricular pacing pulse to disable atrial and ventricular amplifier sensing of the evoked response to the delivered pacing pulse. In addition, a number of sense amplifier refractory periods are timed out on atrial and ventricular sense event signals and generation of A-PACE and V-PACE pulses, such that "refractory" A-EVENT and V-EVENT signals during such refractory periods are selectively ignored or employed in a variety of ways to reset or extend time periods being timed out. Atrial and ventricular refractory periods (ARP and VRP) are commenced upon an A-EVENT or V-EVENT signal or generation of an A-PACE or V-PACE pulse, respectively. The ARP extends through the SAV delay or the PAV delay until a certain time following a V-EVENT signal terminating the SAV or PAV delay or generation of a V-PACE pulse at the expiration of the SAV or PAV delay.

In addition, a post-ventricular atrial refractory period (PVARP) is commenced by a V-PACE pulse or V-EVENT signal so that A-EVENT signals sensed during its time-out are presumed to reflect a retrograde conduction of the evoked or spontaneous ventricular depolarization wave and are ignored and not employed to reset an escape interval and commence an SAV delay. Retrograde conduction is a condition where the depolarization of the ventricles propagates backwards into the atria, causing the atria to depolarize, which atrial depolarization in turn propagates through the AV node into the ventricles, causing the ventricles to depolarize. If retrograde conduction originating from a PVC continues over several cardiac cycles, a tachycardia may result.

Thus, DDD and DDDR pacemaker systems sense and pace in the atrial and ventricular chambers, and pacing is either triggered and inhibited depending upon sensing of intrinsic, non-refractory atrial and ventricular depolarizations during the sequentially timed V-A interval and AV delay, respectively, as is well known in the art. Such DDD and DDDR pacemaker IPGs effectively function in a VDD pacing mode when the sinus atrial heart rate varies within the lower rate and the upper rate limit and such intrinsic atrial depolarizations are consistently sensed. The following description is thus intended to encompass the various types of dual chamber pacemaker systems in which the present invention can be implemented in both implantable pacemakers and in dual chamber ICDs.

Figure 4:
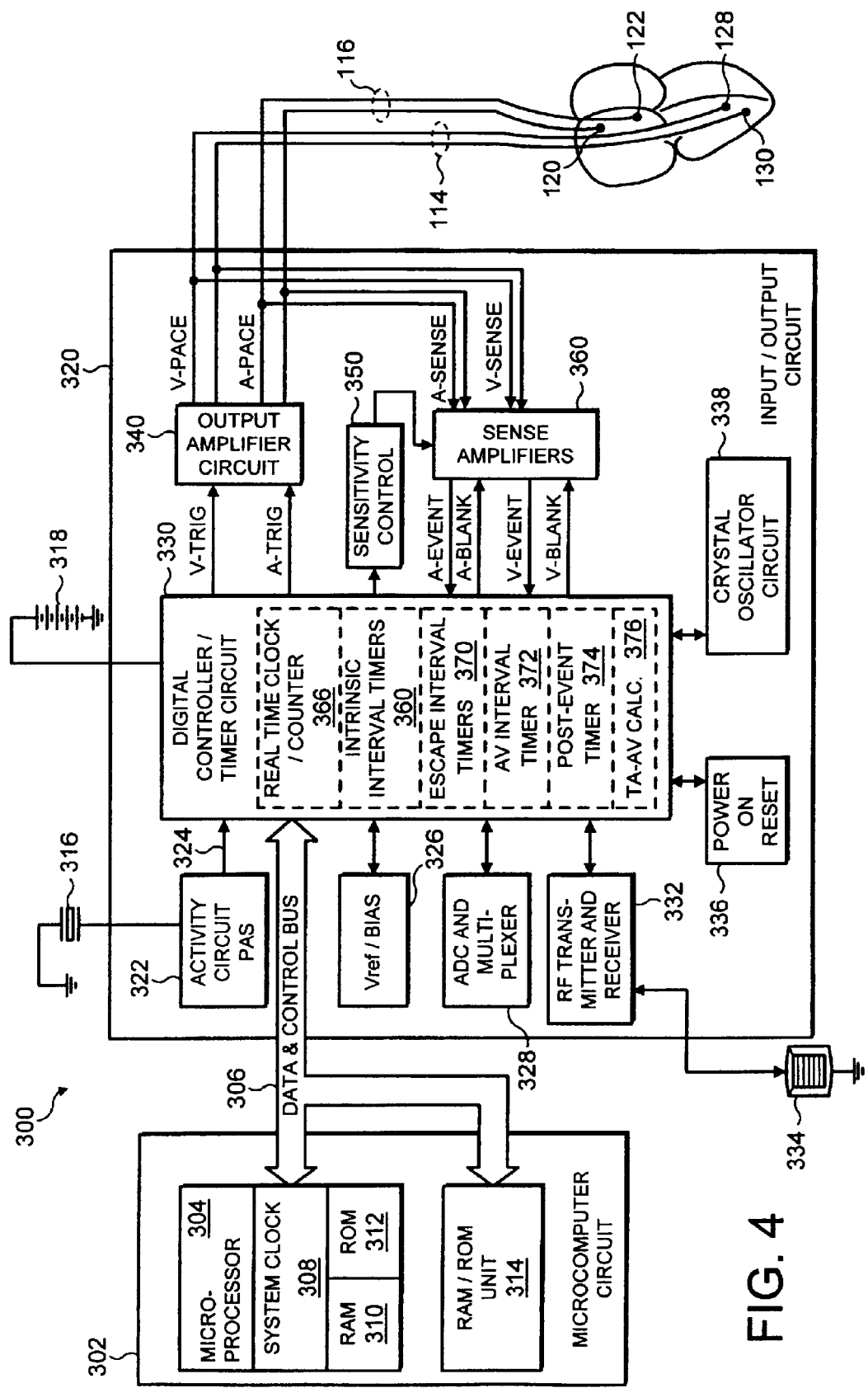
FIG. 4 is a schematic block diagram of major functional blocks of one embodiment of a DDD/DDDR pacemaker operating system that can be employed to carry out the present invention.

The IPG 100 depicted in FIG. 3 is provided with a hermetically sealed enclosure 118, typically fabricated of bio-compatible metal such as titanium, enclosing the dual chamber IPG circuit 300 depicted in FIG. 4. A connector block assembly 112 is mounted to the top of the enclosure 118 to receive electrical connectors located on the proximal connector ends of the depicted bipolar atrial and ventricular pacing leads 114 and 116.

The bipolar atrial pacing lead 116 extends between its proximal connector coupled to IPG 100 and distal atrial pace/sense electrodes 120 and 122 located in the right atrium 12 of heart 10 to sense P-waves and to deliver atrial pacing pulses to the right atria. Atrial pacing pulses may be delivered between electrodes 120 and 122 in a bipolar pacing mode or between electrode 122 and the housing 118 of the IPG 100 in a unipolar pacing mode. Sensing of P-waves may occur between electrode 120 and electrode 122 in a bipolar sensing mode or between either of electrode 120 and 122 and the housing 118 of the IPG 100 in a unipolar atrial sensing mode.

Similarly, the bipolar ventricular pacing lead 114 extends between its proximal connector coupled to IPG 100 and distal ventricular pace/sense electrodes 128 and 130 located in the right ventricle 16 of heart 10 to both sense R-waves and to deliver ventricular pacing pulses to the ventricles. Ventricular pacing pulses may be delivered between electrodes 128 and 130 in a bipolar pacing mode or between electrode 130 and the housing 118 of the IPG 100 in a unipolar pacing mode. Sensing of R-waves may occur between electrodes 128 and 130 in a bipolar sensing mode or between either of electrode 128 and 130 and the housing 118 of the IPG 100 in a unipolar ventricular sensing mode.

In accordance with a preferred embodiment of the invention, the IPG 100 or one of the leads 114 or 116 includes one or more physiologic sensor that is employed to derive a physiologic RCP signal that relates to the need for cardiac output. The use of physiologic sensors to provide variation of pacing rate in response to sensed physiologic parameters, such as physical activity, oxygen saturation, blood pressure and respiration, has become commonplace. Commonly assigned U.S. Pat. Nos. 4,428,378 and 4,890,617, incorporated herein by reference in their entireties, disclose activity sensors which are employed to vary the pacing escape interval in single and dual chamber pacemaker IPGs in response to sensed physical activity. Similarly, the SAV and PAV delays are varied in response to the heart rate and/or the sensor input. As described further below, the TA-AV delay may also be altered during the TA period of FIG. 2A as a function of the RCP derived physiologic pacing rate. Such an activity sensor 316 is coupled to the inside surface of the I PG housing 118 and may take the form of a piezoelectric crystal transducer as is well known in the art.

The preferred embodiment of the IPG 100 preferably operates in a DDD or DDDR pacing mode, described above wherein pacing pulses are delivered to both right atrium 12 and right ventricle 16 in AV synchrony. Sensed atrial and ventricular depolarizations are both effective to inhibit delivery of the next scheduled pacing pulse in the chamber in which they are detected or in any related mode where the AV delay is employed, including the related VDD, DDI, DVI, DVIR and DDIR modes.

Typically, the AV delay in such DDD and DDDR pacemakers is either fixed or varies with the prevailing intrinsic atrial rate, measured as an A-A interval, or a physiologic sensor derived atrial escape interval corresponding to the sensor derived atrial pacing rate. As shown in FIG. 2A, the common AV delay or one or both of the SAV delay and the PAV delay are decremented from an initial implant time interval to a final time interval which is relatively short.

Preferably, during the TA period, the actual TA-AV delay is influenced in a physiologic manner by the same inputs (A-A interval and/or sensor input) as in the 'normal' DDDR mode during the TA time period. In other words, while the TA-AV delay is progressively shortened as shown in FIG. 2A during the TA period toward the final 100 ms AV delay, the prevailing TA-AV delay at any point during the TA period may be shortened further in response to a rate response algorithm responding to the RCP or a high intrinsic atrial heart rate. The TA-AV delay shortening algorithm derives an RA-AV (or RA-PAV and RA-SAV) delay that provides a more physiologic AV delay during exercise affecting the RCP or stress causing the intrinsic heart rate to increase. The degree of alteration of the TA-AV delays are programmable as in any DDDR device.

The IPG circuit 300 within IPG 100 and the bipolar atrial and ventricular leads 114 and 116 are depicted in FIG. 4 in relation to heart 10. The IPG circuit 300 is divided generally into a microcomputer circuit 302 and a pacing input/output circuit 320. The input/output circuit 320 includes the digital controller/timer circuit 330, the atrial and ventricular pacing pulse output circuit 340 and the atrial and ventricular sense amplifier circuit 360, as well as a number of other components and circuits described below. Control of timing and other functions within the input/output circuit 320 is provided by the digital controller/timer circuit 330. Digital controller/timer circuit 330, operating under the general control of the microcomputer circuit 302, includes a set of timing and associated logic circuits, of which certain ones pertinent to the present invention are depicted and described further below.

The atrial and ventricular pacing pulse output circuit 340 and sense amplifier circuit 360 contain pulse generators and sense amplifiers corresponding to any of those presently employed in commercially marketed cardiac pacemakers for atrial and ventricular pacing and sensing. The bipolar leads 114 and 116 are illustrated schematically with their associated electrode sets 120,122 and 128, 130, respectively, as coupled directly to the atrial and ventricular pacing pulse output circuit 340 and sense amplifier circuit 360 of pacing circuit 320.

Digital controller/timer circuit 330 also controls sensitivity settings of the atrial and ventricular sense amplifiers 360 by means of sensitivity control 350 and times out an atrial blanking (A-BLANK) signal and a ventricular blanking (V-BLANK) signal. In the absence of an A-BLANK signal, atrial depolarizations or P-waves in the A-SENSE signal that are detected by the atrial sense amplifier result in an A-EVENT signal that is communicated to the digital controller/timer circuit 330. Similarly, in the absence of a V-BLANK signal, ventricular depolarizations or R-waves in the V-SENSE signal that are detected by the ventricular sense amplifier result in a V-EVENT signal that is communicated to the digital controller/timer circuit 330. The A-EVENT signal is characterized as a refractory A-EVENT signal if it occurs during time-out of an ARP or a PVARP or a non-refractory A-EVENT signal if it occurs after time-out of these atrial refractory periods. Similarly, a V-EVENT signal is characterized as a refractory V-EVENT signal if it occurs during time-out of a VRP or a non-refractory V-EVENT signal if it occurs after time-out of this ventricular refractory period. Refractory A-EVENT signals and V-EVENT signals are typically ignored for purposes of resetting timed out AV delays and V-A intervals, although diagnostic data may be accumulated related to their occurrences.

Digital controller/timer circuit 330 also interfaces with other circuits of the input output circuit 320 or other components of IPG circuit 300. Crystal oscillator circuit 338 provides the basic timing clock and battery 318 provides power for the pacing circuit 320 and the microcomputer circuit 302. Power-on-reset circuit 336 responds to initial connection of the circuit to the battery 318 for defining an initial operating condition and similarly, resets the operative state of the IPG circuit 300 in response to detection of a low battery condition. Reference mode circuit 326 generates stable voltage reference and currents for the analog circuits within the pacing circuit 320. ADC (analog to digital converter) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from an external programmer (not shown) is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. The telemetry transceiver system disclosed in commonly assigned U.S. Pat. No. 5,354,319, incorporated herein by reference, may be employed to provide the uplink and downlink telemetry from and to the implanted medical device in the practice of the present invention.

The activity sensor 316 coupled to the implantable pulse generator housing 118 generates an output signal in response to certain patient activities, e.g. ambulating, that is processed and used as the RCP. If the IPG operating mode is programmed to a rate responsive mode, the patient's activity level developed in the patient activity circuit (PAS) 322 is monitored, and a sensor derived V-A interval is derived proportionally thereto. A timed interrupt, e.g., every two seconds, may be provided in order to allow the microprocessor 304 to analyze the output of the activity circuit PAS 322 and update the basic V-A (or A-A or V-V) escape interval employed to govern the pacing cycle and to adjust other time intervals as described below.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide firmware and additional RAM memory capacity. Microprocessor 304 is interrupt driven, operating in a reduced power consumption mode normally, and awakened in response to defined interrupt events, which may include the A-TRIG, V-TRIG, A-EVENT and V-EVENT signals.

Microcomputer 302 controls the operational functions of digital controller/timer 324, specifying which timing intervals are employed in a programmed pacing mode via data and control bus 306. The specific values of the intervals timed by the digital controller/timer circuit 330 are controlled by the microcomputer circuit 302 by means of data and control bus 306 from programmed-in parameter values. The microcomputer 302 also calculates a number of intervals, including the V-A interval, the AV delay, and the ARP, PVARP and VRP, as a function of the RCP or the intrinsic atrial heart rate. During the TA-period, the TA-AV delay may also be shortened as a function of the RCP or intrinsic atrial heart rate.

The depicted counters and timers within digital controller/timer circuit 330 include a real time counter/timer 366 that is used to time out the TA period and maintain a the count of TA-AV delay adjustments so that the TA-AV or TA-PAV and/or the TA-SAV delay can be periodically adjusted at particular time increments and counts. Digital controller/timer circuit 330 also includes intrinsic interval timers 368 for timing average intrinsic A-A and V-V intervals from A-EVENTs and V-EVENTs, escape interval timers 370 for timing A-A, V-A, and/or V-V pacing escape intervals, and an AV delay timer 372 for timing the SAV delay from a preceding A-EVENT or the PAV delay from a preceding A-TRIG or a common AV delay. Digital controller/timer circuit 330 also includes post-event interval timers 374 for timing the post-event time intervals, including the A-BLANK, V-BLANK, ARP, PVARP and VRP intervals. Finally, digital controller/timer circuit 330 also includes and a TA-AV calculator 376 for calculating the TA-AV delay (or TA-SAV delay and/or TA-PAV delay) that is employed by the AV interval timer 372 as a function of the controlling algorithm and the real time or count provided by the real time timer/counter 366. Digital controller/timer circuit 330 starts and times out these intervals that are calculated by microcomputer circuit 302 for controlling the above-described operations of the atrial and ventricular sense amplifiers in sense amplifier circuit 360 and the atrial and ventricular pace pulse generators in output amplifier circuit 340.

In order to trigger generation of a V-PACE pulse, digital controller/timer circuit 330 generates a V-TRIG signal at the end of a PAV or SAV delay provided by AV delay timer 372. Similarly, in order to trigger an atrial pacing or A-PACE pulse, digital controller/timer circuit 330 generates an A-TRIG signal at the termination of the V-A interval timed out by escape interval timers 370. Typically, digital controller/timer circuit 330 also times out associated intervals including the A-BLANK interval following delivery of an A-TRIG pulse or V-TRIG pulse, during which atrial sensing is disabled, as well as the V-BLANK interval following a V-TRIG atrial pulse, during which ventricular sensing is disabled.

The post-event interval timers 374 time the ARP from an A-TRIG pulse or A-EVENT during which a sensed A-EVENT is ignored for the purpose of resetting the V-A interval. The ARP extends from the beginning of the SAV or PAV delay following either an A-EVENT or an A-TRIG and until a predetermined time following a V-EVENT or a V-TRIG. The post-event interval timers 374 also time the PVARP from a V-TRIG pulse or V-EVENT during which a sensed A-EVENT is also ignored for the purpose of resetting the V-A interval. The VRP is also be timed out by the post-event interval timers 374 after a V-EVENT or V-TRIG signal so that a subsequent, closely following V-EVENT is ignored for the purpose of restarting the V-A interval.

The base ARP, PVARP and VRP that prevails at the lower rate of 60–70 bpm, for example, are either default or programmed parameter values stored in the microcomputer 302. These refractory period parameter values can be fixed for the full operating range of pacing rates between the lower rate and the URL, which may be 120 bpm, for example, or they can be programmed to follow the algorithm for automatically shortening in duration as the paced or intrinsic heart rate increases to ensure that the long refractory periods during the diminishing escape intervals do not cause loss of sensing of valid intrinsic P-waves and R-waves.

The illustrated IPG circuit 300 of FIG. 4 is merely exemplary, and corresponds to the general functional organization of most multi-programmable microprocessor controlled DDD and DDDR cardiac pacemaker IPGs presently commercially available. It is believed that the present invention is most readily practiced in the context of such an IPG, and that the present invention can therefore readily be practiced using the basic hardware of existing microprocessor controlled dual chamber pacemakers, as presently available, with the invention implemented primarily by means of modifications to the software stored in the ROM 310 of the microcomputer circuit 302. However, the present invention may also be usefully practiced any combination of hardware and software or by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacemaker IPG or pacing system of an ICD having an architecture as illustrated in FIG. 4, and a circuit architecture as illustrated in FIG. 4 is not believed to be a prerequisite to enjoying the benefits of the present invention.

Figure 5:
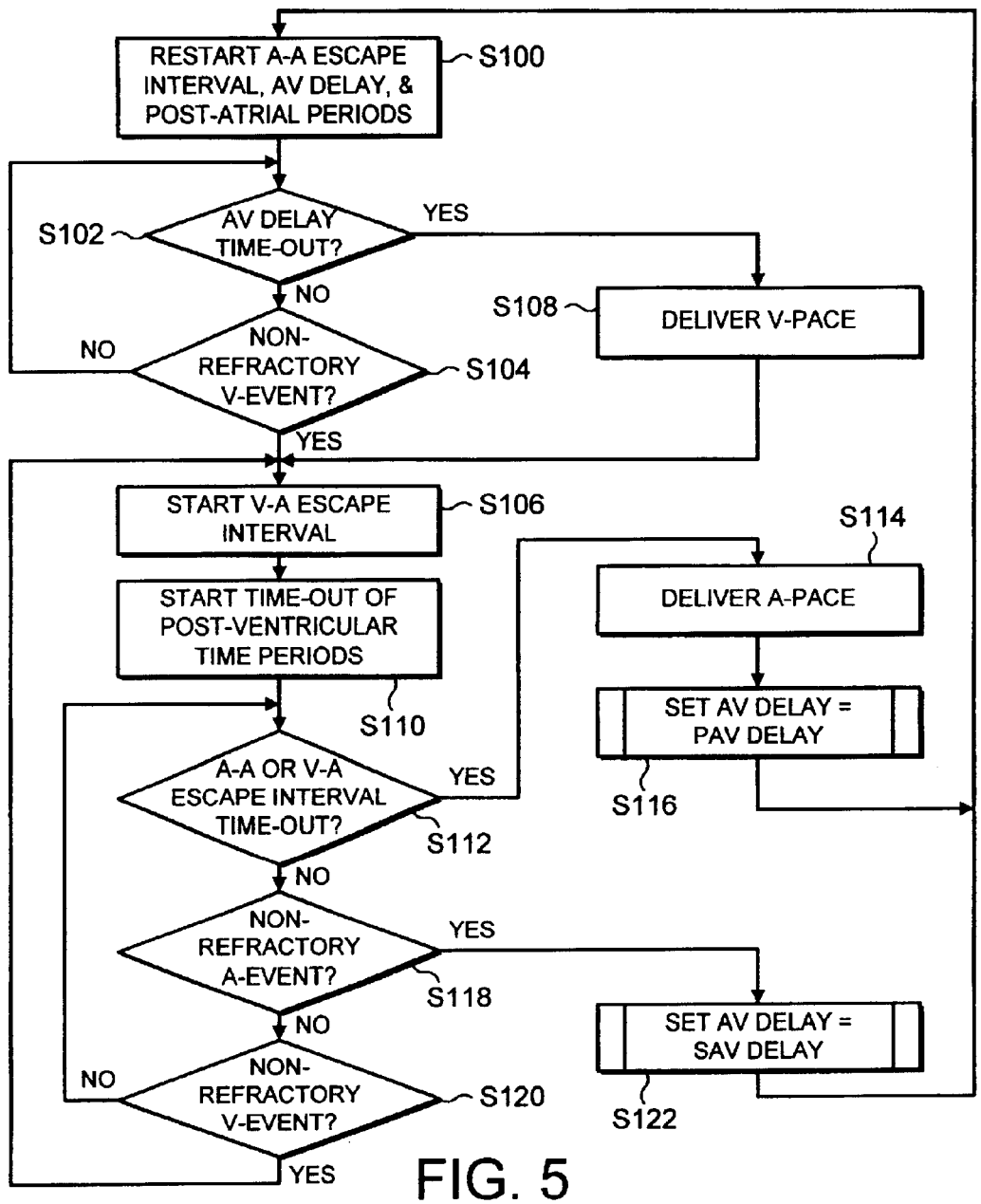
FIG. 5 is a flow chart illustrating the DDD/DDDR pacing mode operating steps in accordance with the present invention.

FIG. 5 is a functional flow chart of the overall pacing cycle timing operation of the DDDR pacemaker IPG illustrated in FIG. 4 in the DDD or DDDR pacing modes. In the flow chart of FIG. 5, it is assumed that the A-A or V-V escape interval, cardiac cycle timing of the IPG ranges between a programmed lower rate and a programmed upper rate limit (URL) and is based on the definition of a V-A interval and an AV delay, specifically either the SAV or the PAV delay. The operations of the flow chart may also incorporate any of the mode switching and sinus preference algorithms of the prior art described above to switch between the use of the sensor or the atrial rate derived escape intervals. The steps depicted in FIG. 5 set forth the primary timing functions and actions of the IPG circuit 300 which recycle continuously. However the algorithm is specifically implemented, it is understood to incorporate the TA-AV delay setting algorithm of the present invention as described hereafter. During the post-implant TA period shown in FIG. 2A, the appropriate TA-AV delay is calculated in steps S116 and S122 as further described in reference to FIGS. 6A and 6B and employed in the operating algorithm depicted in FIG. 5.

At step S100, the V-A interval being timed out in step S112 is reset in response to a non-refractory A-EVENT in step S118 or an A-TRIG in step S116, and timing of the current PAV or SAV delay is commenced. In the flow chart of FIG. 5, it is assumed that the basic timing of the pacing system is based around of the definition of an atrial escape interval (A-A escape interval or V-A escape interval) which may be fixed in the DDD mode or may vary as a function of the RCP. This A-A escape interval, the post-atrial time periods, and the current SAV delay or PAV delay are restarted at step S100 due to an A-EVENT sensed in step S118 or an A-PACE delivered in step S114, respectively, which terminate the V-A escape interval being timed out in step S106. During step S102, the system awaits either time out of the current AV delay (which may be a TA-AV delay during the TA period) or a non-refractory V-EVENT in step S104. The time-out of the AV delay in step S102 is terminated if a non-refractory V-EVENT is sensed at step S104. A V-TRIG is generated and the V-PACE is delivered at step S106 at the end of the AV delay if a non-refractory V-EVENT does not occur at step S104 prior to AV time-out in step S102.

A V-A escape interval is started in step S106 in substitution for the A-A escape interval started in step S100 when either a V-TRIG or a V-EVENT occurs. The post-ventricular time periods, e.g., the PVARP, PVABP, VRP, VBP, URI, are started in step S110 in response to either the time-out of the AV delay or the V-EVENT sensed in step S104. The V-A escape interval started in step S106 or the A-A escape interval set in step S100 continues to time out in step S112, and the atrial and ventricular sense amplifiers are enabled to detect A-SENSE and V-SENSE depolarization waves after the PVABP and VBP, respectively, time out.

The A-TRIG signal is generated by digital controller/timer circuit 330 to trigger delivery of an A-PACE if the A-A or V-A escape interval does time out, as determined in step S112, without a non-refractory A-EVENT or V-EVENT outputted by the atrial or ventricular sense amplifiers. When an A-PACE pulse is delivered in step S114, the next succeeding AV delay is defined to be equal to PAV at step S116, and the A-A escape interval and the PAV delay are restarted at step S100 to commence the next pacing cycle.

The V-A escape interval commenced in step S106 or the A-A escape interval still being timed out in step S100 can time-out in step S112 as described above or be terminated by a non-refractory A-EVENT or V-EVENT output by the atrial or ventricular sense amplifier, respectively, prior to the time-out as determined in step S118 or S120, respectively. If an A-EVENT is provided by the atrial sense amplifier at step S118 prior to expiration of the A-A escape interval or V-A escape interval, then the subsequent AV delay is defined to be equal to SAV at step S122, and the A-A escape interval and the SAV delay are restarted at step S100. The V-A escape interval is restarted in step S106, and steps S110–S122 are repeated if a non-refractory V-EVENT (presumably a PVC) is sensed at step S120 prior to expiration of the escape interval.

Figure 6A:
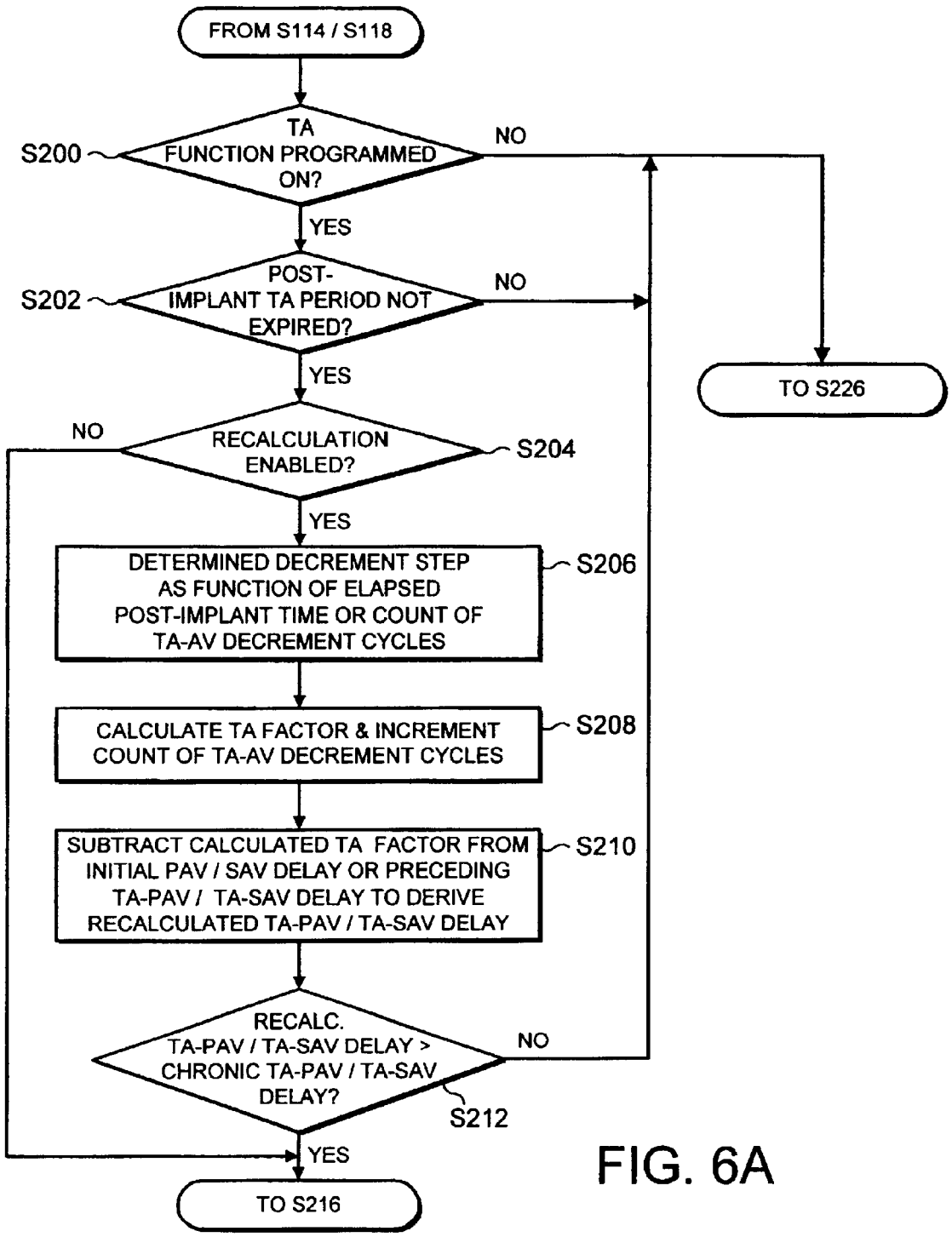
FIGS. 6A and 6B are a flow chart illustrating the calculation of TA-AV delays employed in the DDD/DDDR pacing mode operating steps of FIG. 5.
Figure 6B:
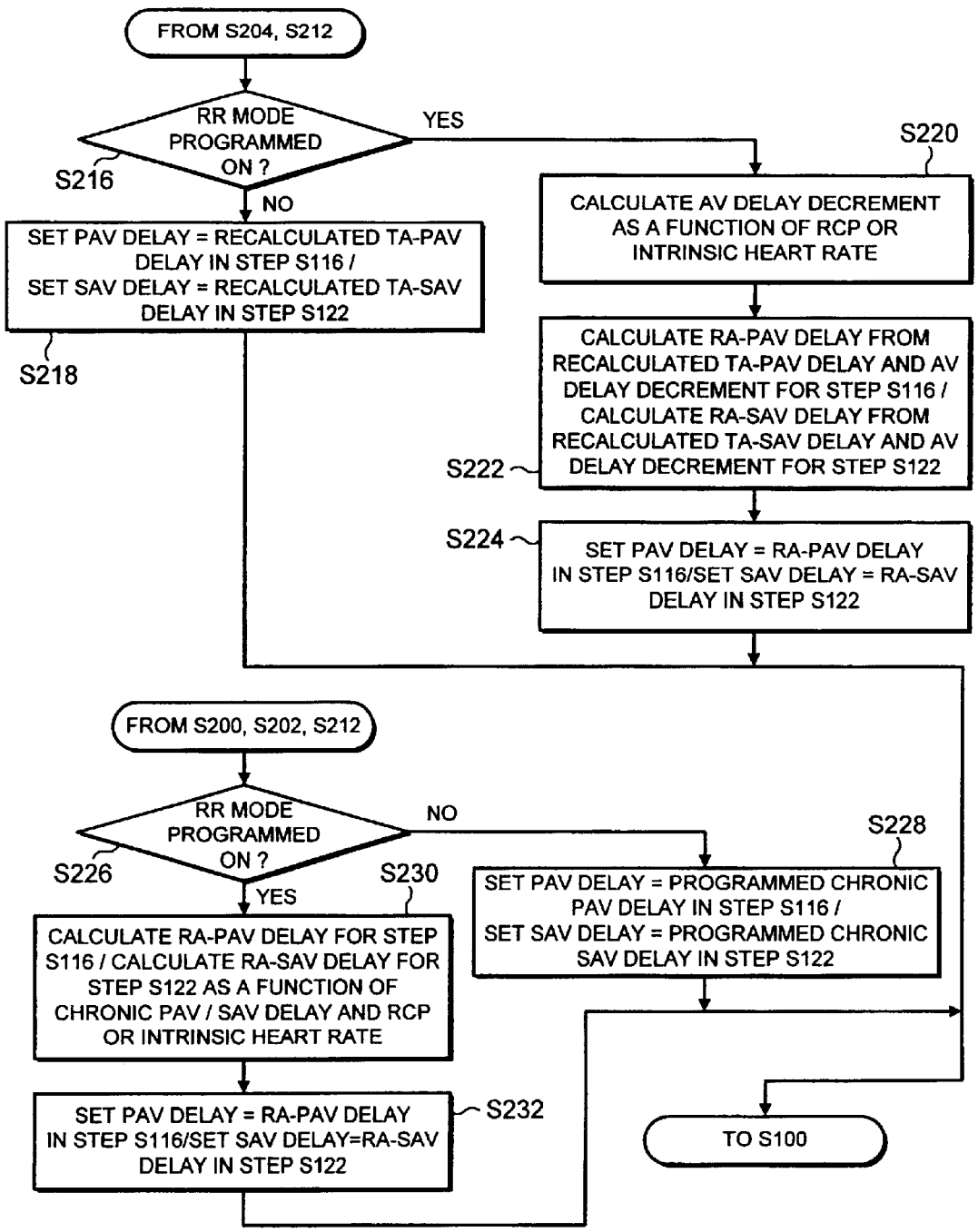
Figure 8:
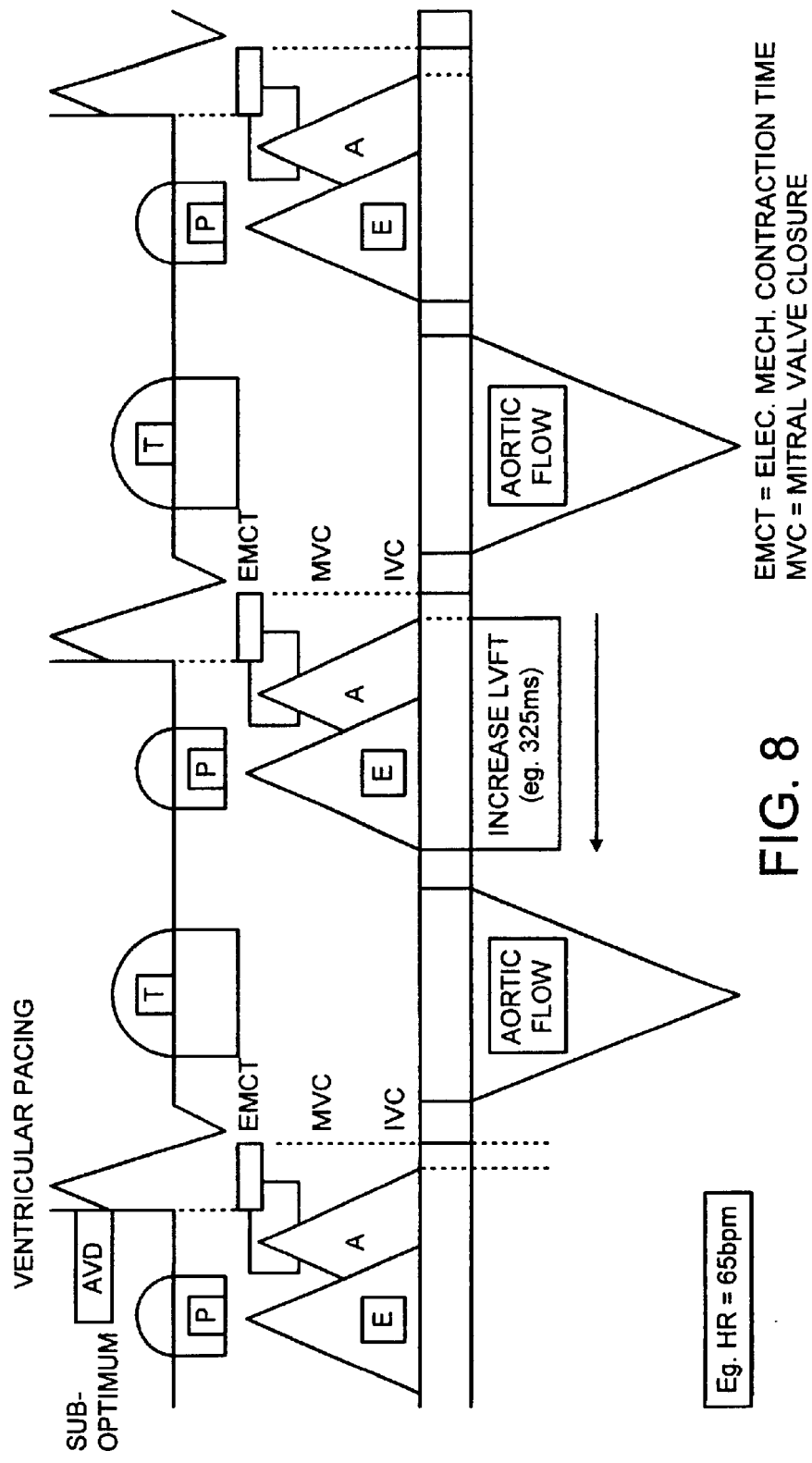
FIG. 8 illustrates a cardiac rhythm evidencing minor LA to LV asynchrony and sub-optimal, too long AV delay timing, partial defusion of E and A waves, and with increased LV Filling (LVFT)

FIGS. 6A and 6B depict steps S116 and S122 in greater detail, particularly showing the periodic recalculation of the TA-PAV delay and the TA-SAV delay in steps S206–S210 when the function is determined to be programmed ON in step S200 and the post-implant TA period has not expired as determined in step S202 and recalculation is otherwise enabled in step S204. The programmed fixed PAV delay and SAV delay (e.g., the 100 ms delay depicted in FIG. 2) of step S202 are employed in step S100 when these conditions are not met and a rate response function (RR) is not programmed ON.

When these conditions of steps S200–S204 are met, the recalculation of the TA-PAV delay and the TA-SAV delay takes place either each time that the program cycles to steps S116 and S122 or once every N times the program cycles to steps S116 and S122. Alternatively, the recalculation of the TA-PAV delay and the TA-SAV delay takes place only once an hour or number of hours or day or number of days or on any periodic schedule that may be programmed as a recalculation time. The recalculation takes place when the programmed recalculation time and/or count occurs as determined in step S206. The last calculated TA-PAV delay and TA-SAV delay is retained in a register in step S210 and employed in steps S114 and S122, respectively, if other conditions of steps S216–S224 of FIG. 6B are satisfied, until they are recalculated.

A TA factor is determined and a the count of TA-AV decrement cycles is incremented in step S208. For example, a decrement step is determined to be appropriate in step S206 when the recalculation time occurs and a TA factor that is other than zero is calculated in step S208. The TA factor can be directly related to the number of TA adjustments that have been made or the actual elapsed post-implant time. The TA factor may be a linear or nonlinear function of the difference between the initially programmed implant AV, PAV and SAV delay (225 ms in the example of FIG. 2A) and the chronic AV, PAV and SAV delay (100 ms in the example of FIG. 2A) and the number of recalculations to be made over the post-implant period or the elapsed time of the post-implant period.

The calculated TA factor is subtracted from the initially programmed AV, PAV and SAV delay (or the last calculated TA-AV delay) in step S210 to derive the recalculated TA-AV delay that is retained until recalculated again. The recalculated TA-AV delay is compared to the fixed or chronic AV delay in step S212, and the recalculated TA-AV delay is supplied to step S216 as long as it is not shorter than the fixed or chronic AV delay. In this way, the TA-AV delay is linearly or non-linearly decremented from the initial AV delay to the chronic AV delay in decrement steps over the post-implant TA period.

As set forth in step S218, the PAV delay is set to the recalculated TA-PAV delay in step S116 and the SAV delay is set to the recalculated TA-SAV delay in step S122 as long as a RR mode is not programmed on as determined in step S216. If a RR mode is programmed on, then a RR-AV delay decrement is calculated as a function of the RCP or intrinsic atrial heart rate in step S220. At most times, there is no need to elevate pacing rate to increase cardiac output, and the calculated RR-AV delay decrement is zero. The RR-AV delay decrement becomes greater than zero only when the RCP or an elevated intrinsic atrial heart rate signify the need for increased pacing rate and cardiac output. The TA-PAV and TA-SAV delays are decremented by the RR-AV delay decrement in step S222 under such conditions requiring increased cardiac output to derive respective RA-PAV and RA-SAV delays that are used in steps S116 and S122, respectively pursuant to step S224. When the RR-AV delay decrements exceed zero, they cause temporary decreases in the TA-PAV and TA-SAV delays as shown, for example, in FIG. 2B.

A similar process takes place to determine the PAV and SAV delays employed in steps S114 and S122 if the conditions of steps S200 or S202 or S212 are not met. Either a RR varying PAV delay and SAV delay or the programmed chronic PAV delay and SAV delay are employed as determined in steps S226–S232.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents listed hereinabove are hereby incorporated by reference into the specification hereof in their respective entireties. As those of ordinary skill in the art will appreciate readily upon reading the Summary of the Invention, Detailed Description of the Preferred Embodiments and Claims set forth herein, at least some of the devices and methods disclosed in those patents may be modified advantageously in accordance with the teachings of the present invention.

We claim:

1. A dual chamber pacing system adapted for pacing a heart in a patient during a post-implant Time-Adaptive period, comprising:

atrial sense means for sensing an atrial signal from an atria of the patient's heart and providing an A-EVENT signal;

AV delay timing means for timing an AV delay from an A-EVENT signal;

ventricular sense means for sensing a ventricular signal from ventricles of the patient's heart and providing a V-EVENT signal;

ventricular pace means for generating and delivering a ventricular pace pulse to the ventricles of the patient's heart at the expiration of the AV delay;

means for setting the AV delay at an initial AV delay at a first time related to the time of implant of the dual chamber pacing system in the patient; and means for providing a Time-Adaptive AV delay during a post-implant Time-Adaptive period that gradually changes the initial AV delay to a chronic AV delay at the end of the post-implant Time-Adaptive period, wherein the initial AV delay is a longer time interval than the time interval of the chronic AV delay.

2. The dual chamber pacing system of claim 1, wherein the means for providing the Time-Adaptive AV delay comprises means for decrementing the Time-Adaptive AV delay in time interval from the time interval of the initial AV delay to the time interval of the chronic AV delay in decrement steps over the post-implant Time-Adaptive period.

3. The dual chamber pacing system of claim 1, wherein the means for providing the Time-Adaptive AV delay comprises means for linearly decrementing the Time-Adaptive AV delay in time interval from the time interval of the initial AV delay to the time interval of the chronic AV delay in decrement steps over the post-implant Time-Adaptive period.

4. The dual chamber pacing system of claim 1, wherein the means for providing the Time-Adaptive AV delay comprises means for non-linearly decrementing the Time-Adaptive AV delay in time interval from the time interval of the initial AV delay to the time interval of the chronic AV delay in decrement steps over the post-implant Time-Adaptive period.

5. A dual chamber pacing system adapted for pacing a heart in a patient during a post-implant Time-Adaptive period, comprising:

atrial sense means for sensing an atrial signal from an atria of the patient's heart and providing an A-EVENT signal;

AV delay timing means for timing an AV delay from an A-EVENT signal;

ventricular sense means for sensing a ventricular signal from ventricles of the patient's heart and providing a V-EVENT signal;

ventricular pace means for generating and delivering a ventricular pace pulse to the ventricles of the patient's heart at the expiration of the AV delay;

means for setting the AV delay at an initial AV delay at a first time related to the time of implant of the dual chamber pacing system in the patient; and means for providing a Time-Adaptive AV delay during a post-implant Time-Adaptive period that gradually changes the initial AV delay to a chronic AV delay at the end of the post-implant Time-Adaptive period, wherein the system is adapted to pace a patient's heart exhibiting CHF/DCM, the initial AV delay being set to an intrinsic AV delay time interval exhibited by the patient's heart, the chronic AV delay being set to a therapeutic AV delay time interval that is shorter than the intrinsic AV delay time interval and alleviates symptoms of the CHF/DCM heart.

6. The dual chamber pacing system of claim 5, wherein the means for providing the Time-Adaptive AV delay comprises means for decrementing the Time-Adaptive AV delay in time interval from the time interval of the initial AV delay to the time interval of the chronic AV delay in decrement steps over the post-implant Time-Adaptive period.

7. The dual chamber pacing system of claim 5, wherein the means for providing the Time-Adaptive AV delay comprises means for linearly decrementing the Time-Adaptive AV delay in time interval from the time interval of the initial AV delay to the time interval of the chronic AV delay in decrement steps over the post-implant Time-Adaptive period.

8. The dual chamber pacing system of claim 5, wherein the means for providing the Time-Adaptive AV delay comprises means for non-linearly decrementing the Time-Adaptive AV delay in time interval from the time interval of the initial AV delay to the time interval of the chronic AV delay in decrement steps over the post-implant Time-Adaptive period.

9. A method of operating a dual chamber pacing system adapted for pacing a heart in a patient during a post-implant Time-Adaptive period, the method comprising:

sensing an atrial signal from an atria of the patient's heart and providing an A-EVENT signal;

timing an AV delay from A-EVENT signal;

sensing a ventricular signal from ventricles of the patient's heart and providing a V-EVENT signal;

generating and delivering a ventricular pace pulse to the ventricles of the patient's heart at the expiration of the AV delay;

setting the AV delay at an initial AV delay at a first time related to the time of implant of the dual chamber pacing system in the patient; and providing a Time-Adaptive AV delay during a post-implant Time-Adaptive period that gradually changes the initial AV delay to a chronic AV delay at the end of the post-implant Time-Adaptive period, the initial AV delay having a longer time interval than the time interval of the chronic AV delay.

10. The method of operating the dual chamber pacing system of claim 9, wherein the Time-Adaptive AV delay is decremented in time interval from the initial AV delay to the chronic AV delay in decrement steps over the post-implant Time-Adaptive period.

11. The method of operating the dual chamber pacing system of claim 9, wherein the Time-Adaptive AV delay is linearly decremented in time interval from the initial AV delay to the chronic AV delay in decrement steps over the post-implant Time-Adaptive period.

12. The method of operating the dual chamber pacing system of claim 9, wherein the Time-Adaptive AV delay is non-linearly decremented in time interval from the initial AV delay to the chronic AV delay in decrement steps over the post-implant Time-Adaptive period.

13. A method of operating a dual chamber pacing system adapted for pacing a heart in a patient during a post-implant Time-Adaptive period, the method comprising:

sensing an atrial signal from the atria of the patient's heart and providing an A-EVENT signal;

timing an AV delay from an A-EVENT signal;

sensing a ventricular signal from the ventricles of the patient's heart and providing a V-EVENT signal;

generating and delivering a ventricular pace pulse to the ventricles of the patient's heart at the expiration of the AV delay;

setting the AV delay at an initial AV delay at a first time related to the time of implant of the dual chamber pacing system in the patient; and providing a Time-Adaptive AV delay during a post-implant Time-Adaptive period that gradually changes the initial AV delay to a chronic AV delay at the end of the post-implant Time-Adaptive period, wherein the system is particularly adapted to pace a patient's heart exhibiting CHF/DCM, the initial AV delay being set to an intrinsic AV delay time interval exhibited by the patient's heart, the chronic AV delay being set to a therapeutic AV delay time interval that is shorter than the intrinsic AV delay time interval and alleviates symptoms of the CHF/DCM heart.

14. The method of operating the dual chamber pacing system of claim 13, wherein the Time-Adaptive AV delay is decremented in time interval from the initial AV delay to the chronic AV delay in decrement steps over the post-implant Time-Adaptive period.

15. The method of operating the dual chamber pacing system of claim 13, wherein the Time-Adaptive AV delay is linearly decremented in time interval from the initial AV delay to the chronic AV delay in decrement steps over the post-implant Time-Adaptive period.

16. The method of operating the dual chamber pacing system of claim 13, wherein the Time-Adaptive AV delay is non-linearly decremented in time interval from the initial AV delay to the chronic AV delay in decrement steps over the post-implant Time-Adaptive period.

17. A dual chamber pacing system adapted for pacing a patient's heart during a post-implant Time-Adaptive period, comprising:

atrial escape interval timing means for timing an atrial pacing escape interval;

atrial pace means for generating and delivering an atrial pace pulse to an atria of the patient's heart at the expiration of the atrial pacing escape interval;

atrial sense means for sensing an atrial signal from the atria of the patient's heart and providing an A-EVENT signal;

AV delay timing means for timing a sense AV (SAV) delay from an A-EVENT signal and a pace AV (PAV) delay from expiration of the atrial pacing escape interval;

ventricular sense means for sensing ventricular signals from ventricles of the patient's heart and providing a V-EVENT signal;

ventricular pace means for generating and delivering ventricular pace pulses to the ventricles of the patient's heart at the expiration of the SAV or PAV delay;

means for setting one or both of the SAV and PAV delay at a time related to the time of implant of the dual chamber pacing system in the patient to one of an initial SAV and PAV delay; and means for providing one or both of a Time-Adaptive SAV delay and PAV delay during a post-implant Time-Adaptive period that gradually changes the initial one of the SAV and PAV delay to a chronic SAV and PAV delay at the end of the post-implant Time-Adaptive period, wherein the initial SAV delay and PAV delay are longer time intervals than the time intervals of the chronic SAV delay and PAV delay.

18. The dual chamber pacing system of claim 17, wherein the means for providing the Time-Adaptive SAV delay and PAV delay comprises means for decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

19. The dual chamber pacing system of claim 18, wherein the means for providing the Time-Adaptive SAV delay and PAV delay comprises means for linearly decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

20. The dual chamber pacing system of claim 18, wherein the means for providing the Time-Adaptive SAV delay and PAV delay comprises means for non-linearly decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

21. A dual chamber pacing system adapted for pacing a patient's heart during a post-implant Time-Adaptive period, comprising:
  atrial escape interval timing means for timing an atrial pacing escape interval;
  atrial pace means for generating and delivering an atrial pace pulse to an atria of the patient's heart at the expiration of the atrial pacing escape interval;
  atrial sense means for sensing an atrial signal from the atria of the patient's heart and providing an A-EVENT signal;
  AV delay timing means for timing a sense AV (SAV) delay from an A-EVENT signal and a pace AV (PAV) delay from expiration of the atrial pacing escape interval;
  ventricular sense means for sensing ventricular signals from ventricles of the patient's heart and providing a V-EVENT signal;
  ventricular pace means for generating and delivering ventricular pace pulses to the ventricles of the patient's heart at the expiration of the SAV or PAV delay;
  means for setting one or both of the SAV and PAV delay at a time related to the time of implant of the dual chamber pacing system in the patient to one of an initial SAV and PAV delay; and
  means for providing one or both of a Time-Adaptive SAV delay and PAV delay during a post-implant Time-Adaptive period that gradually changes the initial one of the SAV and PAV delay to a chronic SAV and PAV delay at the end of the post-implant Time-Adaptive period, the system being adapted to pace a patient's heart exhibiting CHF/DCM, the initial SAV delay and PAV delay being set to an intrinsic SAV delay and PAV delay time interval exhibited by the patient's heart, the chronic SAV delay and PAV delay being set to a therapeutic SAV delay and PAV delay time interval that is shorter than the intrinsic SAV delay and PAV delay time interval and alleviates symptoms of the CHF/DCM heart.

22. The dual chamber pacing system of claim 21, wherein the means for providing the Time-Adaptive SAV delay and PAV delay comprises means for decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

23. The dual chamber pacing system of claim 21, wherein the means for providing the Time-Adaptive SAV delay and PAV delay comprises means for linearly decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

24. The dual chamber pacing system of claim 21, wherein the means for providing the Time-Adaptive SAV delay and PAV delay comprises means for non-linearly decrementing the Time-Adaptive SAV delay and PAV delay in time interval from the time interval of the initial SAV delay and PAV delay to the time interval of the chronic SAV delay and PAV delay in decrement steps over the post-implant Time-Adaptive period.

25. A method of operating a dual chamber pacing system adapted for pacing a patient's heart during a post-implant Time-Adaptive period, the method comprising:
  timing an atrial pacing escape interval;
  generating and delivering an atrial pace pulse to the atria of the patient's heart at the expiration of the atrial escape interval;
  timing a pace AV (PAV) delay from expiration of the atrial escape interval;
  sensing an atrial signal from the atria of the patient's heart and providing an A-EVENT signal;
  timing a sense AV (SAV) delay from an A-EVENT signal;
  sensing ventricular signals from the ventricles of the patient's heart and providing a V-EVENT signal;
  generating and delivering ventricular pace pulses to the ventricles of the patient's heart at the expiration of the SAV or PAV delay;
  setting one or both of the SAV and PAV delay at a time related to the time of implant of the dual chamber pacing system in the patient to one of an initial SAV and PAV delay; and
  providing one or both of a Time-Adaptive SAV delay and PAV delay during a post-implant Time-Adaptive period that gradually changes the initial one of the SAV and PAV delay to a chronic SAV and PAV delay at the end of the post-implant Time-Adaptive period, the initial SAV delay and PAV delays having longer time intervals than the time intervals of the chronic SAV delay and PAV delay.

26. The method of operating the dual chamber pacing system of claim 25, wherein the Time-Adaptive SAV delay and PAV delay is decremented in time interval from the initial SAV delay and PAV delay to the chronic SAV delay and PAV delay in decrement steps over the post-implant Time-Adaptive period.

27. The method of operating the dual chamber pacing system of claim 25, wherein the Time-Adaptive SAV delay and PAV delay is linearly decremented in time interval from the initial SAV delay and PAV delay to the chronic SAV delay and PAV delay in decrement steps over the post-implant Time-Adaptive period.

28. The method of operating the dual chamber pacing system of claim 25, wherein the Time-Adaptive SAV delay and PAV delay is non-linearly decremented in time interval from the initial SAV delay and PAV delay to the chronic SAV delay and PAV delay in decrement steps over the post-implant Time-Adaptive period.

29. A method of operating a dual chamber pacing system adapted for pacing a patient's heart during a post-implant Time-Adaptive period, the method comprising:

timing an atrial pacing escape interval;

generating and delivering an atrial pace pulse to the atria of the patient's heart at the expiration of the atrial escape interval;

timing a pace AV (PAV) delay from expiration of the atrial escape interval;

sensing an atrial signal from the atria of the patient's heart and providing an A-EVENT signal;

timing a sense AV (SAV) delay from an A-EVENT signal;

sensing ventricular signals from the ventricles of the patient's heart and providing a V-EVENT signal;

generating and delivering ventricular pace pulses to the ventricles of the patients heart at the expiration of the SAV or PAV delay;

setting one or both of the SAV and PAV delay at a time related to the time of implant of the dual chamber pacing system in the patient to one of an initial SAV and PAV delay; and providing one or both of a Time-Adaptive SAV delay and PAV delay during a post-implant Time-Adaptive period that gradually changes the initial one of the SAV and PAV delay to a chronic SAV and PAV delay at the end of the post-implant Time-Adaptive period, the system being particularly adapted to pace a patient's heart exhibiting CHF/DCM, the initial SAV delay and PAV delay being set to an intrinsic SAV delay and PAV delay time interval exhibited by the patient's heart, the chronic SAV delay and PAV delay being set to a therapeutic SAV delay and PAV delay time interval that is shorter than the intrinsic SAV delay and PAV delay time interval and alleviates symptoms of the CHF/DCM heart.

30. The method of operating the dual chamber pacing system of claim 29, wherein the Time-Adaptive SAV delay and PAV delay is decremented in time interval from the initial SAV delay and PAV delay to the chronic SAV delay and PAV delay in decrement steps over the post-implant Time-Adaptive period.

31. The method of operating the dual chamber pacing system of claim 29, wherein the Time-Adaptive SAV delay and PAV delay is linearly decremented in time interval from the initial SAV delay and PAV delay to the chronic SAV delay and PAV delay in decrement steps over the post-implant Time-Adaptive period.

32. A method of operating a dual chamber pacing system adapted for pacing a patient's heart during a post-implant Time-Adaptive period, the method comprising:

timing an atrial pacing escape interval;

generating and delivering an atrial pace pulse to the atria of the patient's heart at the expiration of the atrial escape interval;

timing a pace AV (PAV) delay from expiration of the atrial escape interval;

sensing an atrial signal from the atria of the patient's heart and providing an A-EVENT signal;

timing a sense AV (SAV) delay from an A-EVENT signal;

sensing ventricular signals from the ventricles of the patient's heart and providing a V-EVENT signal;

generating and delivering ventricular pace pulses to the ventricles of the patient's heart at the expiration of the SAV or PAV delay;

setting one or both of the SAV and PAV delay at a time related to the time of implant of the dual chamber pacing system in the patient to one of an initial SAV and PAV delay; and providing one or both of a Time-Adaptive SAV delay and PAV delay during a post-implant Time-Adaptive period that gradually changes the initial one of the SAV and PAV delay to a chronic SAV and PAV delay at the end of the post-implant Time-Adaptive period, the Time-Adaptive SAV delay and PAV delay being non-linearly decremented In time interval from the initial SAV delay and PAV delay to the chronic SAV delay and PAV delay in decrement steps over the post-implant Time-Adaptive period.

* * * * *